United States Patent [19]
Sangekar et al.

[11] Patent Number: 5,972,381
[45] Date of Patent: Oct. 26, 1999

[54] SOLID SOLUTION OF AN ANTIFUNGAL AGENT WITH ENHANCED BIOAVAILABILITY

[75] Inventors: Surendra A. Sangekar, Union, N.J.; Ping I. Lee, Radnor, Pa.; Winston A. Vadino, Whitehouse Station, N.J.

[73] Assignee: Schering Corporation, Kenilworth, N.J.

[21] Appl. No.: 08/882,716

[22] Filed: Jun. 25, 1997

Related U.S. Application Data

[60] Provisional application No. 60/020,669, Jun. 28, 1996.

[51] Int. Cl.$^6$ .............. A61K 9/14; A61K 9/20; A61K 9/48
[52] U.S. Cl. ............ 424/451; 424/441; 424/464; 424/465; 424/489; 514/770; 514/772.3; 514/784
[58] Field of Search ..................... 424/441, 451, 424/464, 489, 465; 514/252

[56] References Cited

U.S. PATENT DOCUMENTS
4,791,111   12/1988   Heeres et al. ................ 514/252

FOREIGN PATENT DOCUMENTS
WO 95/17407   6/1995   WIPO.

OTHER PUBLICATIONS
Welling, Peter G. Pharmacokinetics, Process and Mathematics, ACS Monograph 185. American Chemical Society, Washington, DC, Chapter 5, p. 57 (1986).

*Primary Examiner*—James M. Spear
*Attorney, Agent, or Firm*—Thomas D. Hoffman

[57] ABSTRACT

A pharmaceutical composition in the form of a substantially amorphous solid solution comprising an antifungal compound of the formula I:

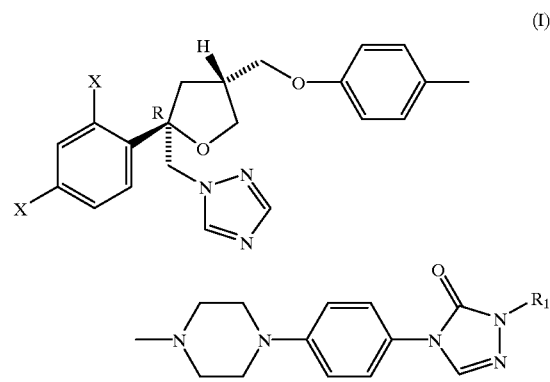

wherein: X is F; and $R_1$ is

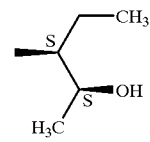

or an ester or ether of said compound of Formula I; and a soluble or insoluble polymer such as: povidone or crospovidone, wherein the ratio of said compound to said polymer is about 1:3 to about 1:6 is disclosed.

2 Claims, No Drawings

SOLID SOLUTION OF AN ANTIFUNGAL AGENT WITH ENHANCED BIOAVAILABILITY

This application claims the benefit of U.S. Provisional Application Ser. No. 60/020,699 filed Jun. 28, 1996.

BACKGROUND OF THE INVENTION

This invention relates to pharmaceutical compositions in the form of a substantially amorphous composition of matter comprising a tetrahydrofuran azole antifungal (as well as esters and ethers thereof) and a polymer used as a polymer matrix.

WO 95/17407, published Jun. 29, 1995, discloses tetrahydrofuran antifungal compounds of Formula (I):

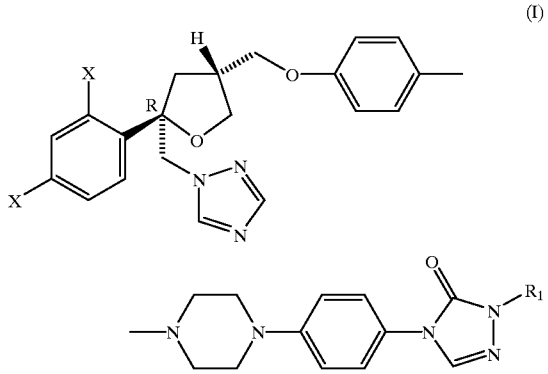

wherein: X is independently both F or both Cl, or one X is independently F and the other is independently Cl; and $R_1$ is a straight or branched chain ($C_3$ to $C_8$) alkyl group substituted by one or two hydroxy moieties; and ethers or esters thereof.

WO 95/17407 discloses that examples of suitable compositions of these compounds include solid compositions such as tablets and capsules. WO 95/17407 discloses that a solid carrier can be one or more substances which may also act as diluents, flavoring agents, solubilizers, lubricants, suspending agents, binders or tablet disintegrating agents; it can also be an encapsulating material. WO 95/17407 discloses that in a tablet, the active compound is mixed with a carrier having the necessary binding properties in suitable proportions and compacted in the shape and size desired.

The oral bioavailability of active compounds can vary with the dosage form of the active compound. For example, it is known that solution dosages and suspensions generally give rise to higher bioavailability than capsules or tablets (see Pharmacokinetics Process and Mathematics, ACS Monograph 185, Chapter 5, page 57 (1986), and J.G. Nairn, Remington's Pharmaceutical Sciences, 18th edition (1990)). However, tablets and capsules are more convenient dosage forms, and it would be preferable to have a tablet or capsule dosage form of an active compound that has good bioavailability.

A pharmaceutical composition of the above described antifungal compounds that provides enhanced bioavailability of the antifungal compounds would be a contribution to the art. A pharmaceutical composition of the above antifungal compounds that can be manufactured in a tablet or capsule form that has greater bioavailability than a suspension would also be a contribution to the art. This invention provides these contributions to the art. Thus, this invention overcomes the problem of making active compounds such as a tetrahydrofuran azole antifungal that have a very low aqueous solubility more bioavailable.

SUMMARY OF THE INVENTION

The present invention provides a pharmaceutical composition comprising a substantially amorphous solid solution, said solid solution comprising:

(a) a compound of the formula I:

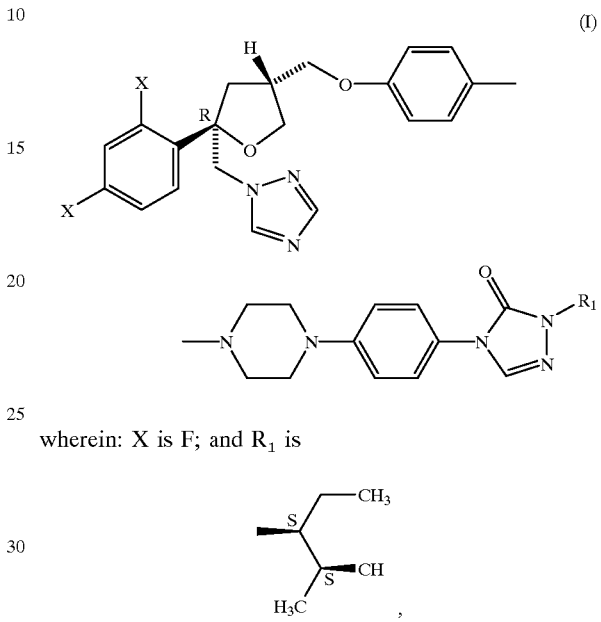

wherein: X is F; and $R_1$ is or an ester or ether of said compound of Formula I; and (b) a polymer selected from the group consisting of: povidone, crospovidone, hydroxypropyl methylcellulose, hydroxypropylcellulose, polyethylene oxide, gelatin, carbomer, carboxymethylcellulose, croscarmellose, methylcellulose, methacrylic acid copolymer, methacrylate copolymer, and water soluble salts such as sodium and ammonium salts of methacrylic acid and methacrylate copolymers, cellulose acetate phthalate, hydroxypropylmethylcellulose phthalate and propylene glycol alginate;

wherein the ratio of said compound to said polymer is about 1:3 to about 1:6.

This invention also provides solid dosage forms comprising the solid solution described above. Solid dosage forms include tablets, capsules and chewable tablets. Known excipients can be blended with the solid solution to provide the desired dosage form. For example, a capsule can contain the solid solution blended with (a) a disintegrant and a lubricant, or (b) a disintegrant, a lubricant and a surfactant. A tablet can contain the solid solution blended with at least one disintegrant, a lubricant, a surfactant, and a glidant. The chewable tablet can contain the solid solution blended with a bulking agent, a lubricant, and if desired an additional sweetening agent (such as an artificial sweetener), and suitable flavors.

DETAILED DESCRIPTION OF THE INVENTION

Unless stated otherwise, wt % is based on the total weight of the composition such that the sum equals 100 wt %.

Reference to the "compound of Formula I" also includes reference to esters, e.g. the glycine ester, and ethers of said compound, unless indicated otherwise.

The term "substantially amorphous solid solution" as used herein means a homogeneous solution of the antifungal compound of Formula I in a polymer matrix, wherein the polymer used as the polymer matrix is (a) soluble polymer (e.g., povidone) wherein the compound of Formula I and the soluble polymer form a homogenous matrix or (b) an insoluble polymer (e.g., crospovidone, wherein the compound of Formula I is molecularly dispersed in the crospovidone polymer i.e. matrix).

The term "substantially amorphous" as applied to solid solutions as used herein means that the solid solutions as measured by x-ray diffraction analysis are greater than 90% amorphous i.e., homogeneous and consist of a single phase.

The present invention includes esters and ethers of the compound of formula I.

For amino acid esters, e.g., the glycine ester of the compound of Formula I, R¹ represents:

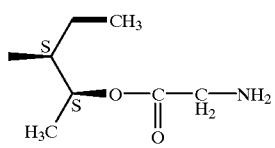

The compound of Formula I is a tetrahydrofuran antifungal compound whose preparation is described in Examples 24 and 32 of WO 95/17407, published 29 Jun. 1995; The preparation of esters and ethers of the compound of formula I are described in W095/17407, published 29 Jun. 1995 and in WO096/38443, published Dec. 5, 1996. The glycine ester of the compound of Formula I is described in Example 33 of copending commonly owned Application Ser. No. 08/460,752 filed on Jun. 2, 1995, U.S. Pat. No. 5,661,151.

The substantially amorphous solid solutions of the antifungal compound of Formula I may be prepared by dissolving said antifungal compound and a soluble polymer in a suitable organic solvent and then removing the solvent to give a solid solution. Said solid solution is a homogeneous matrix of the antifungal compound and the polymer. A preferred pharmaceutical composition contains a solid solution of the antifungal compound of formula I and povidone.

Alternatively, the substantially amorphous solid solutions of the present invention may be produced by dissolving the antifungal compound of Formula I in a suitable organic solvent that will swell an insoluble polymeric matrix, and then absorbing the resulting solution into the insoluble polymeric matrix. The solvent is then evaporated from the resulting mixture. This results in a solid solution that is substantially, i.e. greater than 90%, in an amorphous state wherein the antifungal compound of formula I is molecularly dispersed in the polymeric matrix.

The preparation of solid solutions from soluble polymers is 5 well known in the art; see, for example, page 173 in Kollidon—polyvinylpyrrolidone for the pharmaceutical industry by BASF.

The preparation of solid solutions from insoluble polymeric matrices are also known in the art, and such preparations are similar to those for drug loading into crosslinked hydrogels; see for example, U.S. Pat. No. 4,624,848 and Lee, P.I., Kinetics of Drug Release from Hydrogel Matrices, Journal of controlled Release, Vol. II, pages 277 to 288 (1985).

Suitable polymers for use as the polymeric matrix in said solid solution include soluble and insoluble polymers which are selected from the group consisting of povidone, crospovidone, hydroxypropyl methylcellulose, hydroxypropyl-cellulose, polyethylene oxide, gelatin, carbomer, carboxymethyl-cellulose, croscarmellose, methylcellulose, methacrylic acid copolymer, ammonio methacrylate copolymer, cellulose acetate phthalate, hydroxypropylmethylcellulose phthalate and propylene glycol alginate. Crospovidone and croscarmellose are insoluble polymers; povidone, hydroxypropylmethylcellulose, hydroxypropylcellulose, polyethylene oxide, gelatin, carbomer, carboxymethylcellulose, methylcellulose, methacrylic acid copolymer, methacrylate copolymer, and water soluble salts such as sodium and ammonium salts of methacrylic acid and methacrylate copolymers, cellulose acetate phthalate, hydroxypropylmethylcellulose phthalate and propylene glycol alginate are soluble polymers. All these polymers are well known in the art. Preferably, povidone or crospovidone are used; and more preferably, povidone is used.

Povidone represents 1-vinyl-2-pyrrolidinone polymers (polyvinylpyrrolidone) having a weight average ranging from about 12,000 to about 150,00. Generally, the povidone used has a weight average in the range of about 7000 to about 54,000, with about 28,000 to about 54,000 being preferred, and about 29,000 to about 44,000 being more preferred.

Crospovidone represents water-insoluble synthetic cross-linked homopolymers of N-vinyl-2-pyrrolidinone. Generally, the crospovidone has a particle size of about 20 µM to about 250 µM, and preferably about 50 µM to about 250 µM (see, for example, Kollidon, polyvinylpyrrolidone for the pharmaceutical industry by BASF).

The ratio of the antifungal compound of Formula I to polymer is about 1:3 to about 1:6, preferably about 1:3 to about 1:4, and more preferably 1:4.

The composition comprising the solid solution can, optionally, further comprise excipients selected from the group consisting of: disintegrants, lubricants, surfactants, glidants, artificial sweeteners, bulking agents, colorants and one or more in flavorants.

Generally, the composition comprising the solid solution can, optionally, further comprise: about 8 to about 40 wt % of one or more disintegrants, about 0.5 to about 2 wt % of one or more lubricants, about 4 to about 10 wt % of one or more surfactants, about 0.5 to about 5 wt % of one or more glidants, with about 1 to about 2 wt % being preferred; about 1 to about 10 wt % of one or more artificial sweeteners, about 40 to about 60 wt % of one or more bulking agents, about 0.1 to about 10 wt % of one or more colorants (coloring agents), and/or about 1 to about 5 wt % of one or more flavorants (flavoring agents).

The term "disintegrants" is used herein means any material which is added to pharmaceutical compositions to help break apart such compositions and release the medicament therefrom.

Suitable disintegrants are selected from the group consisting of: croscarmellose sodium (a cross-linked polymer of carboxymethylcellulose sodium, see NF XVII page 1922 (1990)), crospovidone, starches, celluloses, alginates, and gums. Preferably, the disintegrants are selected from croscarmellose sodium or crospovidone. Preferably, croscarmellose sodium is used as the disintegrant in compositions for capsules. Preferably, crospovidone is used as the disintegrant in compressible tablets. Those skilled in the art will appreciate that it is desirable for compressible tablets to disintegrate within 30 minutes; therefore, the disintegrant used preferably results in the disintegration of the tablet within 30 minutes. It has been found that disintegrants, such as croscarmellose sodium and sodium starch glycolate, used in amounts of less than 30 wt % did not produce tablets which disintegrated within 30 minutes. It is believed that significantly higher amounts of such disintegrants would result in a tablet that disintegrates within 30 minutes.

The term "lubricant" as used herein refers to a substance added to the dosage form to enable the dosage form, e.g., a tablet, after it has been compressed to release from the mold or die.

Suitable lubricants include talc, magnesium stearate, calcium stearate, stearic acid, hydrogenated vegetable oils and the like. Preferably, magnesium stearate is used.

The term "surfactant" as used herein refers to surface active agents, especially non-ionic sufactants i.e. a surfactant that lacks a net ionic charge.

Suitable surfactants include polyether glycols such as Pluronic® F-68 (Poloxamer 188), Pluronic® F87 (Poloxamer 237), Pluronic® F108 (Poloxamer 338), and Pluronic® F127 (Poloxamer 407). Preferably, Pluronic® F-68 is used. According to BASF Corporation's Technical Bulletin (1995), Pluronic® is a registered tradename for BASF Corporation's block copolymers of ethylene oxide and propylene oxide represented by the chemical structure $HO(C_2H_4O)_a(C_3H_6O)_b(C_2H_4O)_aH$ wherein for: (a) Pluronic® F-68, a is 80 and b is 27; (b) Pluronic® F87, a is 64 and b is 37; (c) Pluronic® F108, a is 141 and b is 44; and Pluronic® F127, a is 101 and b is 56. The average molecular weights for these block copolymers are: (a) Pluronic® F-68, 8400; (b) Pluronic® F87, 7700; (c) Pluronic® F108, 14600; and Pluronic® F127, 12600.

The term "glidants" as used herein refers to a substance, such as an anticaking agent, which improves the flow characteristics of a powder mixture.

Suitable glidants include silicon dioxide and talc. Preferably, silicon dioxide is used.

The term "bulking agent" as used herein refers to substances (which are also called diluents) that usually make up the major portion of the composition or dosage form.

Suitable bulking agents include xylitol, mannitol, compressible sugars, lactose, and microcrystalline celluloses.

Preferably, xylitol is used for chewable tablets.

Suitable artificial sweeteners include saccharin, cyclamates and aspartame.

If desired known flavorants and known FD & C colorants can be added to the composition.

The composition comprising the solid solution can be reconstituted with water for oral administration. In this dosage form the composition can optionally contain known sweeteners, flavorants, colorants and bulking agents.

The composition comprising the solid solution can be produced in solid dosage forms. Solid dosage forms include capsules (e.g., soft gelatin capsules and hard gelatin capsules) tablets (including, for example, coated tablets, gel coated tablets and enteric coated tablets), and chewable tablets. These dosage forms can be produced by methods well known in the art—see for example Lachman et al., The Theory and Practice of Industrial Pharmacy, 2nd Edition, Lea & Febiger, Philadelphia, pages 321–344 and pages 389–404 (1976).

For capsule dosage forms, the composition comprising the solid solution generally further comprises disintegrants, lubricants, and, optionally, surfactants. Thus, a composition for use in capsules can comprise about 80 to about 90 wt % of the solid solution, about 8 to about 20 wt % of one or more disintegrants, about 0.5 to about 2 wt % of one or more lubricants, and, optionally, about 4 to about 10 wt % of one or more surfactants.

For example, a composition for use in a capsule dosage form comprises: about 80 to about 90 wt % of the solid solution, about 8 to about 20 wt % of one or more disintegrants and about 0.5 to about 2 wt % of one or more lubricants.

Another example of a composition for use in a capsule dosage form is a composition comprising about 80 to about 90 wt % of the solid solution, about 8 to about 15 wt % of one or more disintegrants, about 0.5 to about 2 wt % of one or more lubricants, and about 4 to about 10 wt % of one or more surfactants.

In general, the compositions for capsule dosage forms contain the solid solution, one disintegrant, one lubricant, and optionally, one surfactant.

Preferably, the disintegrant in the capsule compositions is croscarmellose sodium.

For a compressible tablet dosage form the composition comprising the solid solution generally further comprises disintegrants, lubricants, surfactants, and glidants. Thus, a composition for use in compressible tablets can comprise about 50 to about 70 wt % of the solid solution, about 25 to about 40 wt % of one or more disintegrants, with about 30 to about 40 wt % of one or more disintegrants being preferred, about 0.5 to about 2 wt % of one or more lubricants, about 2 to about 10 wt % of one or more surfactants, and about 1 to about 2 wt % of one or more glidants. Preferably, the disintegrant is crospovidone. More preferably, the disintegrant is crospovidone in an amount of about 30 to about 40 wt %. Most preferably, the disintegrant is crospovidone in an amount of about 25 to about 30 wt % and another disintegrant (preferably croscarmellose sodium) is used in amounts of about 5 to about 10 wt %.

When used as a disintegrant, the crospovidone generally has a particle size of about 20 $\mu$M to about 250 $\mu$M, with about 50 $\mu$M to about 250 $\mu$M being preferred.

In addition to the disintegrant, the compressible tablet also preferably comprises one lubricant, one surfactant and one glidant.

For chewable tablets, the composition generally comprises about 40 to about 60 wt % of the solid solution, about 40 to about 60 wt % of a bulking agent (e.g., a sugar such as xylitol), and about 0.5 to about 2 wt % of a lubricant, optionally about 1 to about 10 wt % of an artificial sweetener (e.g., sodium saccharin or aspartame), and optionally about 0.1 to about 10 wt % of a colorant.

A preferred composition for tablets comprises: (1) about 62.5 wt % of a solid solution comprising (a) a compound of Formula I and (b) povidone, wherein the ratio of said compound to said polymer is about 1:4; (2) about 6.25 wt % of croscarmellose sodium (disintegrant); (3) about 25.5 wt % of crospovidine (disintegrant); (4) about 0.625 wt % of magnesium stearate (lubricant); (5) about 3.125 wt % of Pluronic® F-68 (surfactant); and about 2 wt % of silicon dioxide (glidant). More preferably, the povidone has a molecular weight of about 29,000 to about 44,000. A preferred composition is illustrated in Example 13 below.

The examples that follow are intended to exemplify the claimed invention, and such examples should not be construed as limiting the disclosure or the claimed invention.

In the examples that follow, the compound of formula I (hereinafter "compound I" or "I"):

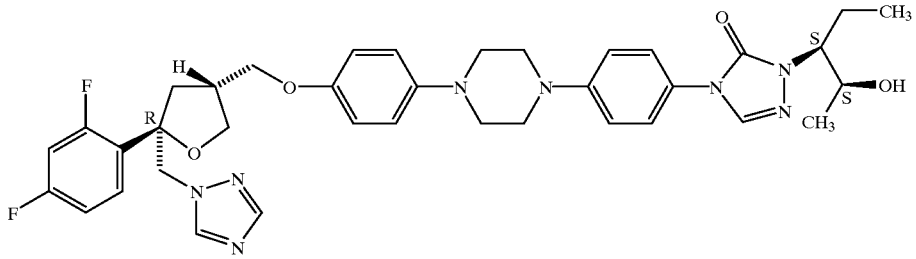

is used; the esters and ethers of I may also be used.

DOSING PROTOCOL FOR DOGS

The formulation to be tested was administered orally to male beagle dogs in a single dose (PO, single). The number of dogs for each test is indicated by the letter "N" followed by an equal sign and a number. Thus, "(N=6)" means the formulation was administered to six dogs. The total amount of the compound of Formula I administered was 200 mg given as two capsules or tablets containing 100 mg each, or one 200 mg tablet. The administered dose (tablet, capsule or control suspension) was slowly washed down with 25 mL of water. Blood samples were taken at 0, 30 minutes, 1 hour, 2 hours, 4 hours, 6 hours, 8 hours, 24 hours, 48 hours and 72 hours. Serum for analysis was obtained after clotting, and centrifugation at 4° C. Serum samples (one per time point) were split and stored at −20° C. until bioassayed as described below.

The feeding schedule for the dogs to be tested was: (1) between noon and 2 PM on the day before drug administration the dogs were fed a half ration of food (15 g/kg); (2) at about 4 PM of the same day as (1) any uneaten food was removed; (3) at about 7:30 AM the next day, about I hour before drug administration, the dogs were fed a half ration of food (15 glkg); (4) about 1 hour after feeding began (about 8:30 AM) the uneaten food was removed and the drug was administered; and (3) after the 4 hour time point after drug administration the dogs were fed normally.

Dogs that were fasted were not given food beginning 18 hours before drug administration and were fed normally after the 4 hour time point after drug administration.

Dogs were fed unless otherwise indicated.

BIOAVAILABILITY ASSAY

Samples of dog serum were collected at selected time intervals. Proteins from the serum samples were precipitated with methanol. The supernatants were analyzed by HPLC/JUV detection procedure using a high pressure liquid chromatograph ($C_{18}$ column) equipped with a ultra violet detector. the $C_{max}$ and AUC (area under the curve, 0–72 hours) values were calculated using standard procedures to determine the bioavailability of the compound in the tested formulations. The larger the AUC value, the greater the bioavailability.

A suspension of the compound of Formula I was used as a control. The control was made by suspending 200 mg of the compound of formula I in 4 mL of a 0.4% (wt/v) solution of methyl cellulose. The 0.4 % methyl cellulose solution was made by adding 4 grams of methyl cellulose to one liter of distilled water and heating at about 80° C. with stirring for about 1½ hours. After about 45 minutes (of the 1½ hours), while heating and stirring, 5.6 ml of Tween 80 and 9 grams of NaCl were added to the methyl cellulose solution. The resulting solution was autoclaved at about 121° C. for about 65 minutes at about 15 lbs. of pressure. The autoclaved solution was cooled for about 30 minutes at room temperature and then stored at 4° C. Gelling occurs at high temperatures, but will clarify when cooled. The solution was stirred or swirled prior to use.

The results of the bioavailability assay are given in terms of $C_{max}$ μg/mL and AUC μg.hr/mL.

EXAMPLE 1

PREPARATION OF SOLID SOLUTION

Composition:

| Ingredient | g/batch |
| --- | --- |
| Compound (I) | 4.0 |
| Povidone K29/32 | 16.0 |
| Methylene Chloride | 200 mL |

Method:

Compound of formula I and the povidone were dissolved in methylene chloride to form a solution. The solvent was evaporated under a hood, and then the residue was dried under a vacuum. The residue was then reduced to fine particles by grinding. The residue was then passed through a 30 mesh screen. The powder was found to be amorphous by x-ray analysis.

EXAMPLE 2

PREPARATION OF SOLID SOLUTION

A solid solution was prepared according to the procedure in Example 1 with the exception that the solution was spray dried using a portable spray drier.

EXAMPLE 3

PREPARATION OF SOLID SOLUTION

A solid solution was prepared according to the procedure in Example 2 with the exception that methanol was used as the solvent instead of methylene chloride.

EXAMPLE 4

PREPARATION OF SOLID SOLUTION

A solid solution was prepared according to the procedure of Example 1 with the exception that the solution was dried using a vacuum double drum dryer.

EXAMPLE 6

PREPARATION OF SOLID SOLUTION

A solid solution was prepared according to the procedure of Example 4 wit h the exception that methanol was used as the solvent.

EXAMPLE 6

PREPARATION OF SOLID SOLUTION

Composition:

| Ingredient | g/batch |
|---|---|
| Compound (I), | 4.0 |
| Povidone K29/32 | 12.0 |
| Methylene Chloride | 200 mL |

Method:

Compound (I) and the povidone were dissolved in methylene chloride to form a solution. The solvent was evaporated under a hood, and then the residue was dried under a vacuum. The residue was reduced to fine particles by grinding. The residue was passed through a 30 mesh screen. The powder was found to be amorphous by x-ray analysis.

EXAMPLE 7

PREPARATION OF SOLID SOLUTION

A solid solution was prepared according to the procedure in Example 6 with the exception that the solution was spray dried using a spray drier.

EXAMPLE 8

PREPARATION OF SOLD SOLUTION

A solid solution was prepared according to the procedure in Example 7 with the exception that methanol was used as the solvent instead of methylene chloride.

EXAMPLE 9

PREPARATION OF SOLID SOLUTION

A solid solution was prepared according to the procedure of Example 6 with the exception that the solution was dried using a vacuum double drum dryer.

EXAMPLE 10

PREPARATION OF SOLID SOLUTION

A solid solution was prepared according to the procedure of Example 9 with the exception that methanol was used as the solvent.

EXAMPLE 11

CAPSULE FORMULATION

Composition

| Ingredient | g/batch |
|---|---|
| Solid Solution ((I):povidone K29/32 = 1:4) | 500 |
| Croscarmellose sodium | 50 |
| Magnesium Stearate | 5 |
| Total | 555 |

Method:

A solid solution having a ratio of Compound I to povidone of 1:4 was prepared by a procedure similar to that of Example 1. The solid solution and coroscarmellose sodium were mixed in a mixer for about 10 minutes. A premix was formed with the magnesium stearate and about an equal portion of the mixture. The premix was added to the mixture and the resulting mixture was further mixed for about 5 minutes. The mixture was encapsulated in No. 0 hard shell gelatin capsules.

Bioavailability in Dogs:

| Bioavailability Parameters | Capsule of Ex. 11 200 mg Dose (N = 6) | Control Suspension 200 mg Dose (N = 8) |
|---|---|---|
| $C_{max}$ (µg/mL) | 1.26 | 0.95 |
| AUC µg · hr/mL | 60.83 | 32.5 |

EXAMPLE 12

CAPSULE FORMULATION

Composition:

| Ingredient | mg/capsule |
|---|---|
| Solid Solution ((I):povidone K29/32 = 1:4) | 500 |
| Croscarmellose sodium | 50 |
| Pluronic ® F-68 | 25 |
| Magnesium Stearate | 5 |
| Total | 580 |

Method:

A solid solution having a ratio of Compound (I) to povidone of 1:4 was prepared by a procedure similar to that of Example 1. The solid solution, croscarmellose sodium and Pluronic® F-68 were mixed in a mixer for about 10 minutes. A premix of magnesium stearate and an equal portion of the mixture was formed. The premix was added to the mixture and the mixture was further mixed for about 5 minutes. The mixture was encapsulated in No. 0 hard shell gelatin capsules.

Bioavailability in Dogs:

| Bioavailability Parameters | Control Suspension 200 mg Dose (N = 12) Fed | Capsule Ex. 12 200 mg Dose (N = 12) Fed | Capsule Ex. 12 200 mg Dose (N = 6) Fasted |
|---|---|---|---|
| $C_{max}$ (µg/mL) | 1.55 | 2.44 | 1.55 |
| AUC µg · hr/mL | 66.39 | 97.25 | 62.83 |

EXAMPLES 13, 14 AND 15

TABLET FORMULATIONS

Compositions

| Ingredient | Ex. 13 mg/tab | Ex. 14 mg/tab | Ex. 15 mg/tab |
|---|---|---|---|
| Solid Solution ((I):povidone K29/32 = 1:4) | 500 | 500 | 1000 |
| Pluronic ® F-68 | 25 | 50 | 50 |
| Silicon dioxide | 16 | 16 | 32 |
| Croscarmellose Sodium | 50 | 50 | 100 |
| Crospovidone | 204 | 204 | 408 |
| Magnesium Stearate | 5 | 5 | 10 |
| Total | 800 | 825 | 1600 |

Method:

The solid solution was prepared by a procedure similar to that of Example 2. The solid solution was compacted using a compactor and milled through an 18 mesh screen. The remainder of the excipients, except for the magnesium stearate, were added and mixed in a suitable mixer for about 15 minutes. A premix of magnesium stearate with an equal portion of the mixture was made. The premix was added to the mixture and mixed for about 5 minutes. The resulting mixture was then compressed into tablets using a single station tablet machine.

Bioavailability in Dogs:

| Bioavailability Parameters | Control Suspension 200 mg Dose (N = 24) | Tablet Ex. 13 200 mg Dose (N = 6) | Tablet Ex. 15 200 mg Dose (N = 6) |
| --- | --- | --- | --- |
| $C_{max}$ (μg/mL) | 1.31 | 1.81 | 1.33 |
| AUC μg · hr/mL | 53.41 | 66.31 | 56.11 |

EXAMPLE 16
CHEWABLE TABLET

Composition:

| Ingredient | mg/tab |
| --- | --- |
| Solid Solution ((I):povidone K29/32 = 1:4) | 1000 |
| Xylitol | 990 |
| Magnesium Stearate | 20 |
| Total | 2010 |

Method:

A solid solution, made by procedures similar to that of Example 2, was mixed with the xylitol in a suitable mixer for about 10 minutes to form a mixture. A premix was made with the magnesium stearate and an equal portion of the mixture. The premix was added to the remainder of the mixture and mixed further for about 5 minutes. The mixture was compressed into tablets using a single station tablet machine.

EXAMPLE 17
SOLID SOLUTION

Composition:

| Ingredient | g/batch |
| --- | --- |
| Compound (I) | 10 |
| Crospovidone | 40 |
| Methylene Chloride | 50 mL |

Method:

Compound (I) was dissolved in methylene chloride. While mixing, the solution of Compound (I) was slowly added to the crospovidone until all the solution was absorbed. The resulting solid solution was vacuum dried The residue was reduced to fine particles by grinding. The residue was then passed through a 30 mesh screen. The powder was found to be substantially amorphous by x-ray analysis.

EXAMPLE 18

CAPSULE FORMULATION

Composition:

| Ingredient | mg/capsule |
| --- | --- |
| Solid Solution ((I):povidone K29/32 = 1:4) | 500 |
| Croscarmellose sodium | 50 |
| Pluronic ® F-68 | 25 |
| Magnesium Stearate | 5 |
| Total | 580 |

Method:

A solid solution, made by procedures similar to that of Example 17, was mixed with the above ingredients, except for the magnesium stearate, in a suitable mixer for about 10 minutes. A premix was made of the magnesium stearate and an equal portion of the mixture. The premix was added to the remainder of the mixture and the resulting mixture was mixed for about 5 minutes. The mixture was encapsulated into No. 0 hard shell gelatin capsules.

Bioavailability in Dogs:

| Bioavailability Parameters | Control Suspension 200 mg Dose (N = 24) | Capsule of Ex. 18 200 mg Dose (N = 6) |
| --- | --- | --- |
| $C_{max}$ (μg/mL) | 1.31 | 2.39 |
| AUC μg · hr/mL | 53.41 | 95.36 |

EXAMPLE 19

COMPARATIVE EXAMPLE

CAPSULE FORMULATION WITHOUT SOLID SOLUTION

Composition:

| Ingredient | mg/capsule |
| --- | --- |
| Compound (I), micronized | 100 |
| Microcyrstalline cellulose | 178 |
| Sodium lauryl sulfate | 22.5 |
| Sodium starch glycolate | 45 |
| Magnesium Stearate | 4.5 |
| Total | 350 |

Method:

Compound (I) which was micronized, microcystalline cellulose, sodium lauryl sulfate and sodium starch glycolate were mixed together in a suitable mixer for about 10 minutes. A premix was made of the magnesium stearate and an equal portion of the mixture. The premix was added to the remainder of the mixture and the resulting mixture was mixed for about 5 minutes. The mixture was encapsulated in No. 0 hard gelatin capsules.

Bioavailability in Dogs:

| Bioavailability Parameters | Control Suspension 200 mg Dose (N = 8) | Capsule of Ex. 19 200 mg Dose (N = 6) |
|---|---|---|
| $C_{max}$ (µg/mL) | 0.95 | 0.95 |
| AUC µg · hr/mL | 32.5 | 29.72 |

It is generally recognized that micronized drugs have a higher bioavailability. However, the above data demonstrate that the conventional capsule formulation of Example 19 with its micronized compound, as well as the control suspension of Example 20 hereinbelow with its micronized compound, have a lower bioavailability compared to the solid solution formulations of this invention represented by Examples 11 and 12 and the tablet formulations represented by Examples 13 and 15.

EXAMPLE 20

COMPARATIVE EXAMPLE

CONTROL SUSPENSION IN FASTED DOGS

The following data are for fasted dogs.

| Bioavailability Parameters | Control Suspension 100 mg Dose (N = 5) | Control Suspension (with 200 mg tartaric acid) 200 mg Dose (N = 6) |
|---|---|---|
| $C_{max}$ (µg/mL) | 0.18 | 0.33 |
| AUC µg · hr/mL | 5.21 | 12.0 |

The above data demonstrate that the control suspensions of Example 20 have a lower bioavailability in fasted dogs than the control suspensions in fed dogs--see Examples 11, 12, 13, and 18. This difference in bioavailability (fed versus fasted) is much greater with the control suspensions of this Example than with the solid solution compositions of this invention (see Example 12 for example).

While the present invention has been described in conjunction with the specific embodiments set forth above, many alternatives, modifications and variations thereof (e.g. use of esters and ethers of I) will be apparent to those of ordinary skill in the art. All such alternatives, modifications and variations are intended to fall within the spirit and scope of the present invention.

What is claimed is:

1. A pharmaceutical composition comprising a substantially amorphous solid solution, said solid solution comprising:

(a) a compound of the formula:

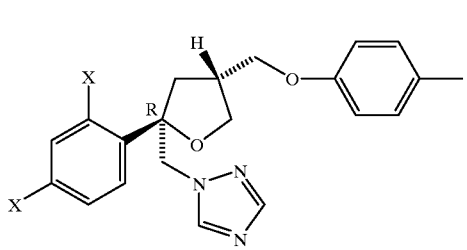
(I)

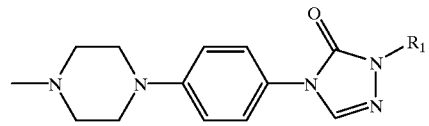

wherein: X is independently F; and $R_1$ is

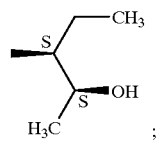

and (b) the polymer selected from povidone or crospovidone; wherein the solid solution comprises about 50 to about 70 wt % of the pharmaceutical composition and wherein the ratio of the compound to the polymer is about 1:3 to about 1:4; and wherein the remaining about 30 to about 50% of the pharmaceutical composition further comprises:
(b) about 25 to about 30 wt % of crospovidone;
(c) about 5 to about 10 wt % of croscarmellose sodium;
(d) about 0.5 to about 2 wt % of magnesium stearate;
(e) about 2 to about 10 wt % of the compound of the formula $HO(C_2H_4O)_{80}(C_3H_6O)_{27}(C_2H_4O)_{80}H$;
(f) about 1 to about 2 wt % of silicon dioxide;

such that the total wt % is 100% based on the weight of the composition.

2. A composition of matter comprising:

(A) about 62.5 wt % of a substantially amorphous solid solution, said solid solution comprising:

(a) a compound of the formula I:

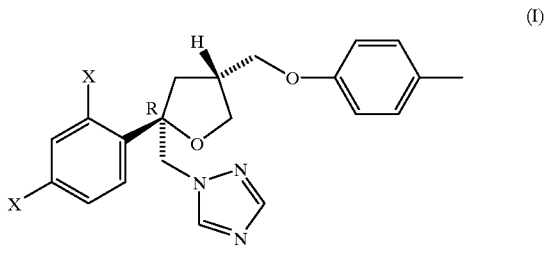
(I)

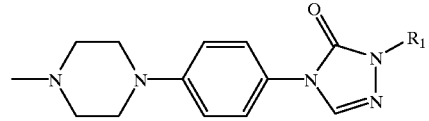

wherein each X is F, and $R_1$ is

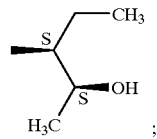

or a pharmaceutically acceptable salt thereof; and (b) povidone; wherein the ratio of said compound to said povidone is about 1:4;

(B) about 25.5 wt % of the disintegrant crospovidone;
(C) about 6.25 wt % of the disintegrant croscarmellose sodium;
(D) about 0.625 wt % of the lubricant magnesium stearate;
(E) about 3.125 wt % of the surfactant Pluronic F-68;

and
(F) about 2 wt % of the glidant silicon dioxide;
such that the total wt % is 100% based on the weight of the composition.

* * * * *